(12) United States Patent
McGlone et al.

(10) Patent No.: US 9,044,395 B2
(45) Date of Patent: Jun. 2, 2015

(54) PHEROMONE COMPOSITIONS AND THEIR USE TO MODIFY BEHAVIOR IN DIFFERENT VERTEBRATE SPECIES

(71) Applicant: Sergeant's Pet Care Products, Inc., Omaha, NE (US)

(72) Inventors: John McGlone, Lubbock, TX (US); Larry Nouvel, Plano, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 13/623,279

(22) Filed: Sep. 20, 2012

(65) Prior Publication Data

US 2013/0071337 A1 Mar. 21, 2013

Related U.S. Application Data

(60) Provisional application No. 61/536,673, filed on Sep. 20, 2011.

(51) Int. Cl.
| | |
|---|---|
| *A61K 9/12* | (2006.01) |
| *A61K 31/568* | (2006.01) |
| *A61K 9/00* | (2006.01) |

(52) U.S. Cl.
CPC ............. *A61K 9/12* (2013.01); *A61K 31/568* (2013.01); *A61K 9/008* (2013.01)

(58) Field of Classification Search
None
See application file for complete search history.

(56) References Cited

U.S. PATENT DOCUMENTS

| | | | |
|---|---|---|---|
| 5,272,134 A | 12/1993 | Berliner | |
| 6,384,252 B1 * | 5/2002 | Pageat | 554/223 |
| 2006/0252738 A1 | 11/2006 | Avelino et al. | |
| 2006/0269513 A1 | 11/2006 | Dodd | |
| 2007/0048230 A1 | 3/2007 | Parsadayan | |
| 2007/0048231 A1 | 3/2007 | Parsadayan | |
| 2010/0242859 A1 * | 9/2010 | Raymond | 119/719 |
| 2011/0150822 A1 | 6/2011 | Nouvel et al. | |
| 2013/0072570 A1 * | 3/2013 | McGlone et al. | 514/703 |

FOREIGN PATENT DOCUMENTS

WO   WO 9206675 A1 * 4/1992

OTHER PUBLICATIONS

McGlone, "Aerosolized 5a-androst-16-en-3-one Reduced Agonistic Behavior and Temporarily Improved Performance of Growing Pigs", Journal of Animal Science, 63:679-684, 1986.*
Meredith, "Distinctive Responses in the Medial Amygdala to Same-Species and Different-Species Pheromones", The Journal of Neuroscience, 24(25), 5719-5725, 2004.*
Markham Animal Clinic, "Cat Behavior Problems", Markham Animal Clinic, www.myvetonline.com/markhamac, 2008, hereafter MarkhamAC.*
Crown Street Veterinary Hospital, "Breeding dogs", www.crownvet.com.au/breeding.html, May 28, 2008.*
McGlone, "Reduction of Pig Agonistic Behavior by Androstenone", J. Anim. Sci., 66:880-884, 1988.*

* cited by examiner

*Primary Examiner* — Robert T Crow
*Assistant Examiner* — John P Nguyen
(74) *Attorney, Agent, or Firm* — Polsinelli PC

(57) ABSTRACT

A composition comprising an INTEROMONE® is described for the modification of undesirable or harmful stress-related behaviors or other behaviors or physiology in a variety of vertebrate species, as well as methods of using the compositions in vertebrates from a species different than the species in which the INTEROMONE® is a naturally occurring pheromone.

13 Claims, 1 Drawing Sheet

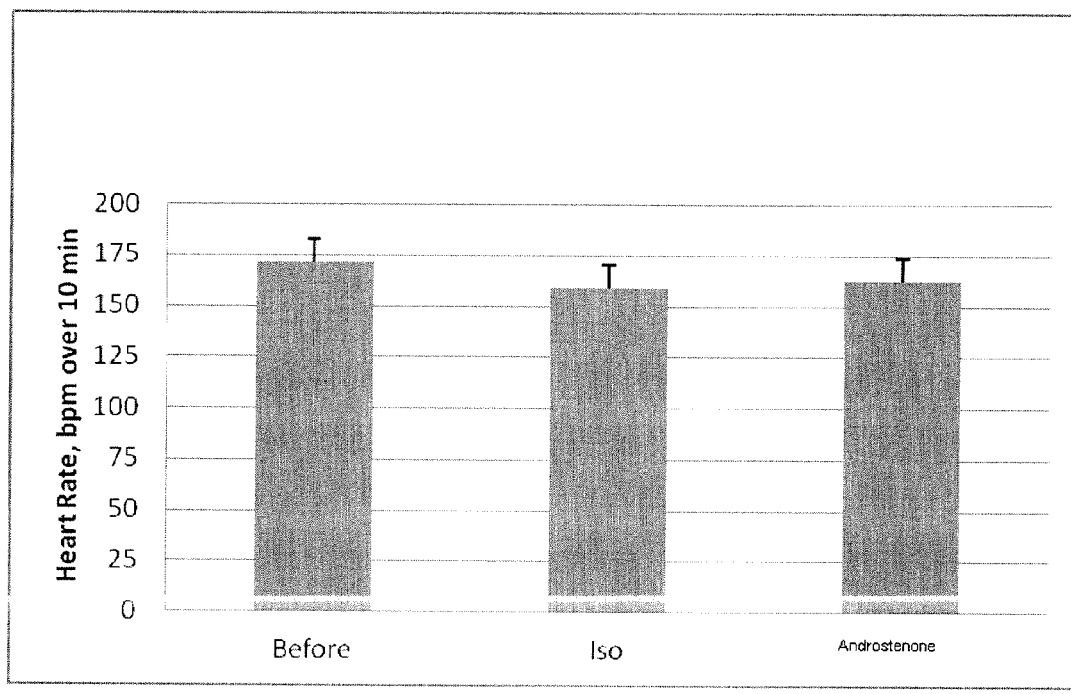

PHEROMONE COMPOSITIONS AND THEIR USE TO MODIFY BEHAVIOR IN DIFFERENT VERTEBRATE SPECIES

RELATED APPLICATION

This application relates to and claims the priority of U.S. Provisional Patent Application No. 61/536,673, which was filed Sep. 20, 2011 and is hereby incorporated by reference in its entirety.

FIELD OF THE INVENTION

The present disclosure is broadly concerned with the field of animal behavior and the use of pheromones and INTEROMONE® compositions. More particularly, the present disclosure is concerned with the use of the pheromone Androstenone as an INTEROMONE® to produce a different behavioral or physiological effect (such as a calming or behavioral-altering effect) in a different vertebrate species from which the pheromone is produced, for example, such as in dogs, cats, snakes, birds, or horses.

BACKGROUND OF THE INVENTION

Pheromones are chemicals released by living organisms that send information to other organisms of the same species via scent. Pheromones are released in response to stress, alarm, danger, sexual fertility, and in other behavioral contexts. Pheromones, by definition and according to evolutionary theory, are species-specific, that is, they are effective in eliciting an innate response only in members of the same species.

Androstenone (also known as 5-α-androst-16-en-3-one) is a steroid found in a number of vertebrate species but is especially pronounced in the male domestic or wild pig. Androstenone acts as a pig sexual pheromone in that the sexually receptive female will seek the boar and express lordosis behavior in the presence of Androstenone or an intact male pig. Androstenone, the odor of an adult dominant male, also reduces aggressive behavior in younger pigs (McGlone, J. J. and J. L. Morrow. 1988. Reduction of pig agonistic behavior by Androstenone. J. Animal Science. 66:880-884). Androstenone is documented as a social pheromone in the pig that changes adult pig behavior and physiology within the same species.

Chemicals that provide interspecies communication are called allelochemicals. Some compounds are known to be a pheromone in one species, but have been observed to have strong behavioral effects in other species. For example, chemicals produced and released by one species that affect the behavior or physiology of another species to the benefit of the originator but not the receiver are known in the art as allomones (See Gras switz, T. R. and G. R. Jones (2002). "Chemical Ecology". Encyclopedia of Life Sciences. John Wiley & Sons, Ltd. doi:10.1038/npg.els 0.0001716). The production of allomones in natural environments has been mainly observed in plant species, which utilize allomones for example to protect plants against insect herbivores.

A kairomone is another known allelochemical. It is emitted by one species and benefits another species, but does not benefit and often harms the emitter. The production of kairomones in natural environments has been mainly observed in insect species. For example, the Ponderosa Pine tree produces a terpene called myrcene when the Western pine beetle damages the tree. The emission of this chemical then lures more beetles to the tree (See Wyatt, T. D. (2003). Pheromones and Animal Behaviour: Communication by Smell and Taste, First Edition (Cambridge, UK: Cambridge University Press).

A synomone is an allelochemical produced and released by one species that benefits both the emitter and receiver. For example, plants emit odors that work to attract bees. The bees are attracted to the plants to feed and then the bees take the pollen to fertilize other plants/flowers.

Accordingly, the allelochemicals known in the art involve the observation of chemicals produced by one species having an effect on another species to the benefit and/or detriment of the emitting or receiving species. What is described is an allelochemical that affects the behavior and/or physiology of another species (i.e., the receiving species) without additionally having a beneficial or harmful effect on the emitting species and having a novel or unrelated behavioral or physiological effect on the receiving species.

For instance, while domestic dogs are known to bark as part of their normal method of communication, dogs may show excessive barking/jumping/mobbing/begging in response to external cues or due to boredom. Mobbing includes repetitive barking and jumping. Certain dogs will bark and jump in an excitable manner when they hear or see people, animals, vehicles, or machines. One theory is that excessive barking is part of the "mobbing" behavior that pack animals have when they attack a prey species (Lord et al., Barking and mobbing., Behav. Processes, 81:358-368, 2009).

Methods used in the art to stop the barking/jumping/begging syndrome have included shock collars, odor sprays, and loud noises, all of which work by startling or distracting the dog from engaging in the undesirable behavior. Dog appeasing pheromones, including synthetic compositions believed to replicate certain calming pheromones emitted by dogs, have also been used in the art to treat certain behavioral problems in dogs, but to date, have not been successful in alleviating the barking/jumping syndrome exhibited by certain dogs. Moreover, the pheromones used in the art have not been directed for use with animal species other than the species from which the pheromones are emitted.

Accordingly, it would be desirable to provide methods and compositions comprising a compound known to be a pheromone in one species to positively modify animal behavioral problems in a variety of different vertebrate species. In particular, there is a need in the art for use of an INTEROMONE® to calm, sedate, reduce anxiety, or otherwise positively modify the behavior of a variety of vertebrate species, including the barking/jumping/begging syndrome exhibited by some dogs or to calm anxious dogs or cats or other vertebrate species.

SUMMARY OF THE INVENTION

It is an object of the present invention to provide novel methods and compositions for the modification of behavior in vertebrate species comprising compounds that have been isolated from one vertebrate species but, surprisingly, have the effect of modifying the behavior in a different vertebrate species. Specifically, certain pheromones have been identified which can be made into compounds and used as part of a method to have cross-species effects as INTEROMONE® compositions. An INTEROMONE® is any naturally secreted or synthetically produced chemical emitted as a pheromone within one species, which, when isolated and administered to a member of a different vertebrate species, elicits a change in behavior or physiology of the different species without the requirement of benefiting and/or harming the species from which the chemical is released.

The present disclosure is specifically concerned with the INTEROMONE® Androstenone and its use in various compositions to effect a modification of behavior in a variety of vertebrates, for example dogs, horses, cats, snakes, and birds. Androstenone is an odorous pheromone used by the domestic pig in sexual/courtship and social behaviors. It was surprising to learn through the present invention that Androstenone has powerful effects on other species, such as dogs, and was observed to change dog behavior.

The compositions of the invention may optionally include other ingredients as necessary or desired, depending on the form and intended use of the final product. Such optional ingredients can include, but are not limited to, carriers such as water, alcohols, solvents, and the like; fragrances, coloring agents, preservatives, antioxidants, and the like. Examples of the resultant product include, but are not limited to, an aerosol or a spray. Alternatively, the resultant product may be a diffuser, collar, spraying collar, foam, dip, wipe, cream, gel, lotion, or fabric garment.

Another object of the present invention is to provide a method for modifying or positively affecting the behavior of a vertebrate, the method comprising administering a composition comprising an INTEROMONE®, such as Androstenone, in an amount effective to affect the behavior of a particular vertebrate, wherein the vertebrate whose behavior is being modified is different than that from which the INTEROMONE® is emitted as a pheromone.

Another object of the present invention is to provide for use of a formulation comprising an INTEROMONE® to positively affect the behavior (e.g. calm) in a different vertebrate species. It is both unexpected and surprising that a chemical known to be a pheromone in one species can have a strong positive behavioral or physiological effect on members of other vertebrate species since pheromones are, by definition, functional only within a particular species.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIG. 1 is a graphic representation of a comparative test to determine whether treatment with Androstenone spray increased dogs' heart rate.

DETAILED DESCRIPTION OF THE INVENTION

The broad term, INTEROMONE®, is used herein to refer to chemicals emitted as pheromones within one vertebrate species that influence the behavior or physiology of a different species without the requirement of benefiting and/or harming the emitter or receiving species (although an INTEROMONE® could benefit or harm the emitting or receiving species). The surprising use of specific pheromones having a cross-species effect without providing any benefit or harm to the emitting species has not heretofore been developed.

The present invention relates to the use of Androstenone in a composition as an INTEROMONE®, rather than as a pig pheromone as it is known and used in the art, in order to affect the behavior of different vertebrate species (such as, for example, dogs, cats, horses, frogs, snakes, birds, etc.). One of skill in the art will appreciate that additional pheromones not specifically disclosed herein may be found to have differential and perhaps beneficial effects in other species, such as pheromones from other mammals (e.g., cats, tigers, lions, elephants, hamsters, mice, and rats), pheromones from reptiles (e.g., snakes and lizards), pheromones from birds, or pheromones from amphibians. Androstenone has been formulated into a composition as an INTEROMONE® for administration to different species (such as, for example, the horse, dog, cat, and other vertebrates) in order to positively modify the behavior of members of the different species.

In particular, administration of Androstenone as an INTEROMONE® to dogs surprisingly results in reducing activity or positively modifying the behavior of dogs that exhibit the anxious behaviors.

The present disclosure provides for a composition comprising an INTEROMONE®, which is a chemical or compound related thereto emitted by one species and known to be a pheromone within that species to modify the behavior of different vertebrate species. When the composition comprising the INTEROMONE® is applied to or in the vicinity of different vertebrate species, the animal is calmed for a period of time. It is unexpected and surprising that a natural compound found in one vertebrate species can have a large, meaningful effect on members of another vertebrate species since pheromones are, by definition, species-specific. 2-methylbut-2-enal (as disclosed in U.S. application Ser. No. 13/623,279, filed on Sep. 20, 2012) and Androstenone are two examples that work in a cross-species manner. Other chemicals and their cross-species beneficial use may become apparent to those skilled in the art following the teachings of the present invention.

I. Formulations

The formulations of the present invention may comprise a chemical that is naturally secreted, isolated from a secretion, or synthetically duplicated from a vertebrate species. The chemicals that may be used in accordance with the present invention are those that produce a certain effect within the species from which they are secreted and a different effect when used in another species.

The formulations of the present invention comprise an INTEROMONE®. In a preferred embodiment, the androgen steroid known as Androstenone is used as an INTEROMONE®. The Androstenone used in the compositions may be the natural pheromone secreted or isolated directly from a male pig, or a synthesized compound characterized by the following structural formula (Including enantiomers, diastereomers, or racemates thereof):

Formula I

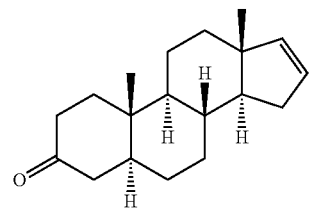

Compounds related to Androstenone that could also be used in accordance with the present invention include, but are not limited to, androstenol, androstadienone, and estratetraenol. The amount of Androstenone in the formulation will be an amount effective to positively modify or alter the behavior (e.g., calm, reduce nervousness, or lower the heart rate) of a particular animal. Generally, the amount of Androstenone in the formulation should be at least 0.001% (w/w) of the total composition. In one embodiment, the concentration of Androstenone in the composition ranges from between about 0.001% to about 1% (w/w). In another embodiment, the concentration of Androstenone in the composition ranges from between about 0.01% to about 0.1% (w/w). Preferably, the concentration of Androstenone present in the composition ranges from between about 0.01% to about 0.05% (w/w) and most preferably the concentration of Androstenone in the composition is about 0.01% (w/w).

In one embodiment, the composition of the present invention contains Androstenone. In another embodiment, the composition contains a combination of Androstenone and at least one additional pheromone composition. For instance, the composition may comprise Androstenone and at least one additional pheromone composition, such as the composition described in U.S. Publication No. 2011/0150822.

In addition to an INTEROMONE®, the formulations may optionally contain additional components such as solvents, propellants, surface-active agents, thickeners, and fragrances (i.e., "additional components"). The formulation may include one additional component or a combination of any of the forgoing additional components in varying amounts. Suitable examples of each type of additional component are detailed below.

In a preferred embodiment, the formulation includes at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. For example, an INTEROMONE® can be dissolved in a suitable alcohol and supplied in a liquid form such as a pump spray or for use in a plug-in diffuser. Suitable alcohols include ethanol, propanol, isopropanol, butanol, pentanol, hexanol, heptanol, octanol, and phenyl ethyl alcohol. In a preferred embodiment, the alcohols comprise ethanol, isopropanol, butanol, and phenyl ethyl alcohol. An alcohol solvent can be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In a preferred embodiment, the solvent is a combination of water and an alcohol selected from the group consisting of ethanol or isopropanol. In a one embodiment, the amount of solvent present in the composition ranges from between about 0.5% and 99.99% (w/w) of the composition. Preferably, the amount of water present in the composition ranges from between about 70% and about 99.99% (w/w) of the composition and most preferably ranges from between about 80% and about 98.5% (w/w). Preferably the amount of alcohol present in the composition ranges from between about 1% and about 20% (w/w) and most preferably ranges from between about 1.5% and about 10% (w/w).

The formulation may additionally include a propellant. Suitable propellants include chlorofluorocarbons (CFC) such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluoroethane, chlorodifluoroethane, difluoroethane, and heptafluoropropane; hydrocarbons such as propane, butane, and isobutene; and compressed gases such as nitrogen, carbon dioxide, and nitrous oxide, as well as combinations of any of the above described propellants. In one embodiment, the propellant is propane. In another embodiment, the propellant is 1,1-difluoroethane. The propellant does not comprise an inert gas of Tumorigen compound class, which includes 1,1,1,2-tetrafluoroethane, chlorodifluoromethane, and dichlorodifluoromethane. Preferably, the propellant has a flash point of less than about −50° C. Generally, when a propellant is included in the composition, such will range from between about 75% to about 99.99% (w/w) of the composition, preferably between about 85% and about 99.99% (w/w), and most preferably from between about 95% and about 99.99% (w/w).

The formulation may optionally include one or more surface-active agents (also called surfactants). Surfactants are generally used in preparing those embodiments of the present invention directed to compositions that are formulated as emulsions. Either water in oil or oil in water emulsions may be formulated. Examples of suitable surfactants include: nonionic ethoxylated and nonethoxylated surfactants, abietic acid, almond oil PEG, beeswax, butylglucoside caprate, C18-C36 acid glycol ester, C9-C15 alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-C12-C13 pareth-3 sulfate, tri-C12-C15 pareth-6 phosphate, and trideceths.

In certain applications, it may be desirable to thicken the formulation. Suitable examples of thickening or viscosity increasing agents, include agents such as: acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxypropyl starch, isopropyl palmitate, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. The amount of thickener present in the formulation may range from between about 1% to about 30% (w/w), preferably from between about 5% to about 20% (w/w), and most preferably from between about 10% to about 15% (w/w).

The composition may additionally comprise a fragrance. The fragrance may be any fragrance that provides a desired odor masking effect since a particular INTEROMONE® may have a pungent odor. Although a variety of fragrances may be employed without departing from the scope of the present invention, suitable fragrances include floral essences, citrus blossoms, oil or extracts of conifers, or spices. Examples of floral essences include rose, lilac, lavender, gardenia, and jasmine. Suitable citrus blossoms include orange and lemon, and suitable oil or extracts of conifers include pine and juniper. Generally, fragrance may comprise between about 0.25% and about 1% (w/w) of the composition.

II. Routes of Administration

Mammals, including dogs, have several anatomical organs that receive olfactory signals. The two most dominant "smell" organs are the main olfactory epithelium (MOE) and the vomeronasal organ (VNO). Other sensory fibers are in the nasal cavity that can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons. Among all the genes in the mammalian body, the olfactory receptors have the largest number of genes. This indicates the importance of olfactory communication in animals, some of which seems to be lost in humans.

Administration of the INTEROMONE® composition to a subject animal is typically accomplished through any method allowing for delivery of an effective amount of the INTEROMONE® via inhalation by the animal. Such methods of administration include, for example, placing or distributing the composition comprising the INTEROMONE® in the environment of the animal, either by incorporating the composition into a wearable device such as a collar, or by applying (e.g. spraying or wiping) the composition to surfaces in the living environment of the animal or directly onto the animal, such as to its facial region or head. For example, the INTEROMONE® composition may be administered topically to an animal using an aerosol, pump spray, foam, collar, wipe, dip, liquid, gel, lotion, and/or cream. The term "effective amount" describes an amount of INTEROMONE® present in a composition that is sufficient to produce a noticeable modification, i.e. improvement, of animal behavior in the subject animal, as determined according to behavioral observations as described herein. The effective amount will depend on factors such as the severity of the behavior being treated; individual animal parameters including age, physical condition, size and weight; concurrent treatments; the frequency of treatment; or the mode of administration. These factors are well known to those of ordinary skill in the art and can be addressed with no more than routine experimentation.

In one embodiment, the INTEROMONE® can be incorporated in various ways as are generally well known into a solid carrier material to form a collar or tag, and the collar or tag is then worn by the animal. The solid carrier material is selected from among those materials, typically polymeric compounds, generally recognized to be suitable for release of active compounds and set forth in further detail herein below. Alternatively, the INTEROMONE® can be combined with a solvent to form a liquid solution and the liquid solution can be further prepared in various formulations suitable for delivery to the animal by inhalation. For example, liquid solutions can be further prepared according to methods well known in the art such as a pump spray, aerosol, gel, foam, shampoo, dip, cream, lotion, gel, diffuser, or spot-on formulation.

In one embodiment, Androstenone is dissolved or diluted in a nonaqueous organic solvent or solvent mixture to form a solution for incorporation into a pump spray containing the INTEROMONE®. The solution may optionally be combined with at least one additional pheromone/INTEROMONE® or pheromone/INTEROMONE® composition. A preferred pump spray solution will comprise about 0.01% (w/w) Androstenone, about 10% (w/w) isopropyl alcohol and about 89% (w/w) water. Additionally, between about 0.5% and 1% (w/w) of a fragrance may be added to the solution.

In another embodiment, Androstenone is dissolved or diluted with a solvent and combined with a propellant to form a solution for incorporation into an aerosol spray composition containing the INTEROMONE®. A preferred aerosol spray solution will comprise about 0.01% (w/w) Androstenone, about 2% (w/w) ethanol, and about 97% (w/w) propane. Additionally, between about 0.5% and 1% (w/w) of a fragrance may be added to the solution.

In an alternative embodiment, Androstenone is dissolved or diluted with a solvent and a thickener to form a solution for use in a diffuser. The solution may optionally be combined with at least one additional pheromone/INTEROMONE® or pheromone/INTEROMONE® composition. A preferred diffuser solution will comprise about 0.02% (w/w) Androstenone, between about 80% to about 85% (w/w) solvent, about 15% (w/w) thickener. Additionally, between about 0.25% and 1% (w/w) of a fragrance may be added to the solution.

In an additional embodiment, the INTEROMONE® may be incorporated into a solid carrier material to form a matrix composition containing the INTEROMONE® (or INTEROMONE® combined with at least one additional pheromone/INTEROMONE® or pheromone/INTEROMONE® composition), such as a fabric garment or a collar. The matrix containing the INTEROMONE® may be formed into a collar as is well known and amply described in the art, for example in U.S. Pat. No. 3,852,416. Typically an admixture of an active (i.e., an INTEROMONE®) and a carrier material providing the matrix is formed into strips through an extrusion process, and each strip is then formed a collar by including a fastening device such as a buckle, snap or hook. The solid carrier material forming the matrix into which the INTEROMONE® is incorporated is for example a polymer or polymer mixture with suitable release characteristics such that the pheromone is released from the collar to be inhaled by the animal. Additionally, the matrix containing the INTEROMONE® may be formed into a fabric garment as is described in the art, for example in U.S. Publication No. 2010/00319632. The INTEROMONE® preferably contributes from between about 0.001% and about 1% (w/w), and preferably between about 0.01% and 0.5% (w/w) of the collar or fabric garment.

Suitable polymers for forming a solid substrate for making a collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer. The polymers can contribute between about 50% to about 99.99% (w/w) of the collar, and typically will contribute between about 90% and about 99.99% (w/w) of the collar. Plasticizers can be incorporated into the mixture to render the polymer resin more flexible. Suitable plasticizers include phosphoric acid esters (e.g. tricresyl phosphate) or phthalic acid esters (such as dioctyl phthalate or diisodecyl phthalate (DIDP)). The collar may also include other additives such as stabilizers, for example antioxidants to protect the collar material from degradation by UV light and other oxidizing factors. Lubricants, colorants, and fillers may also be included.

III. Methods of Using an INTEROMONE® to Modify Behavior in an Animal

The present invention is further directed to a method of using INTEROMONE® compositions to positively modify undesirable or inappropriate behaviors (e.g., barking, jumping, begging, and/or mobbing) or physiology in an animal by exposing the animal to an effective amount of an INTEROMONE®-based composition, wherein the composition comprises at least about 0.001% (w/w) of an INTEROMONE®. Generally, the composition comprises between about 0.001% and about 1% (w/w) of an INTEROMONE®. The animal can be exposed to the composition by any method allowing inhalation by the animal over a period of time sufficient to effect a modification of the target behavior, as determined according to behavioral observations. Typically, depending on the chosen route of administration, the particular animal, and situation, the exposure of the composition to the animal will be over a period of at least one second, but can also be for a period of at least one hour, for a period between one hour and five hours, for a period of at least one day, for a period of at least one week, for a period of between one week and four weeks, for a period of at least one month, or for any period of time as may be needed to achieve a satisfactory behavioral effect. For example, an animal suffering from a temporarily induced anxiety (e.g., a trip to a veterinary office, being handled, or fireworks), may require a brief exposure to the composition before, during or after the anxiety-inducing event to relieve the anxiety and associated behavior. In contrast, an animal exposed to a stressful stimulus for a longer and continual period, such as a pet exposed to a new pet in the household, may benefit from regular exposure to the INTEROMONE® composition for an extended period.

Commonly recognized sources of stress in animals include for example weaning, transportation (especially in motorized vehicles), boredom, lack of exercise, separation anxiety, loud noises, events that induce barking/jumping/begging or anxiety, introduction to new people or animals, and visits to a veterinary office. Animals that are stressed by exposure to such events or conditions will typically exhibit highly undesirable stress-related behavioral symptoms. Such undesirable behaviors are commonly recognized and include for example fearful behavior such as cowering or shaking; excessive chewing, barking, begging, pacing, or excessive laying down; hyperactivity such as jumping; aggressive behavior toward people or other animals such as growling, snappishness or biting; property destruction; and frequent urination or soiling. The efficacy of the INTEROMONE® composition can be tested for example by spraying subject animals with an aerosol spray incorporating the composition, having the subject animals wear a collar incorporating the composition, or by applying the composition in the form of a liquid diffuser or the like in a physical area associated with the stress-inducing conditions for any given animal. In any case, the composition is sufficiently volatile for the animal to inhale and thus be exposed to a sufficient amount of the composition to produce a noticeable behavioral effect. For example, a reduction in undesirable outward behaviors is readily ascertainable (e.g. noticeable reduction in aggressive displays, barking and/or jumping) and can be supplemented by observing other physical indicators of stress such heart rate, weight changes, and secretion of stress hormones such as cortisol. When undesirable behaviors are observed, the composition of the present invention may be used to induce a temporary state of lower activity, calm and reduced excitability.

In use, the composition comprising an INTEROMONE® can be implemented in a number of different ways depending in part on the targeted animals and behavior desired to be modified. A liquid solution containing an INTEROMONE® can simply be applied directly to the coat or skin of the animal, or sprayed on surfaces or objects in the animal's environment, or diffused or sprayed into the air in the animal's environment. For example, an exemplary liquid spray formulation containing Androstenone (dissolved in a suitable solvent) can be sprayed, for example, on the animal's nostrils, face, or head, or in its environment such that it may be perceived through olfaction as frequently as needed to obtain the desired behavioral modification. Alternatively, an INTEROMONE® in liquid, gas, or solid form can be incorporated in a plasticized material such as PVC or the like that can then be formed into a tag, or in strips to form a collar. Furthermore, the INTEROMONE® composition can be combined with at least one additional pheromone/INTEROMONE® or pheromone/INTEROMONE® composition (natural or synthetic) prior to implementation into any of the above-mentioned modes of delivery to the animal.

It should be understood that the INTEROMONE® used in the composition may be provided in the form of pure concentrate (100% concentration) or a diluted composition with additional excipients in the dosage form (i.e. the amount of active ingredient in the composition is less than or equal to 99.99%, and the remainder consists of inactive excipients). If diluted, the amount of INTEROMONE® dispensed in the various dosage forms may range from between about 1.0 pg/mL to about 1.0 g/mL, more preferably between about 1.0 ng/mL to about 1.0 g/mL. One of skill in the art will appreciate that the volume of active component added to the composition will need to be adjusted to account for the dilution and to ensure the end composition comprises the appropriate final concentration of INTEROMONE®. One of skill in the art will also appreciate that the various components of the composition may be provided in a variety of dosage forms including, but not limited to liquid solution or suspension, emulsion, aerosol, slow release matrices, and the like.

The compositions according to this invention may be applied in a variety of ways but are best applied by exposing the olfactory system by any means such as, for example, spraying a light mist directly on the facial region or in the environment of the animal whose behavior is intended to be modified. Further, the methods of the current invention are best accomplished by allowing the animal to inhale the composition, as the nasal cavities, sinuses, lungs and throats of animals present a large area for the aromatic molecules to be bound to an olfactory receptor. The application of the composition to the animal or the animal's environment may be repeated as often as necessary to modify the animal's behavior.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, "a" and "an" mean one or more, unless otherwise indicated.

As used herein, "INTEROMONE®" means any naturally secreted or synthetically produced chemical released by one species, which, when administered to a member of a different vertebrate species, elicits a change in behavior or physiology of the different species with or without providing a benefit or harm to the species from which the chemical is released.

As used herein, "vertebrate" or "vertebrate species" is interchangeable with the word "animal" or "animal species" and encompasses any group of animals distinguished by possession of a vertebral column. Examples of vertebrate species include, but are not limited to, domestic animals such as cats and dogs; small animals, such as hamsters, rabbits, ferrets, rats, mice, and guinea pigs; commercial animals, such as horses, sheep, cattle, and swine; animals in captivity, such as apes, chimpanzees, tigers, lions, bears, elephants, zebras; amphibians such as frogs and salamanders; reptiles such as snakes, turtles, crocodiles, alligators, and lizards; birds, and the like.

Although the invention described herein is susceptible to various modifications and alternative iterations, specific embodiments thereof have been described in greater detail above. It should be understood, however, that the detailed description of the use of Androstenone is not intended to limit the invention to the specific embodiments disclosed. Rather, it should be understood that the invention is intended to cover all modifications, equivalents, and alternatives falling within the spirit and scope of the invention as defined by the claim language.

EXAMPLES

Example 1

Preparation of Aerosol Spray Composition Containing Androstenone for Use on Dogs An aerosol composition comprising Androstenone was prepared in accordance with the formulation set forth in Table 1.

TABLE 1

| Aerosol Spray with Androstenone | | |
|---|---|---|
| Ingredient | % | grams |
| Androstenone | 0.01 | 0.01 |
| Ethanol | 2.00 | 2.00 |
| Propane (propellant) | 97.99 | 97.99 |
| Total | 100.00% | 100 |

Example 2

Determining the Efficacy of an Aerosol Spray Composition Containing Androstenone as an INTEROMONE® to Modify Behavior of Dogs An aerosol spray composition comprising Androstenone solution was prepared in accordance with Example 1, but was then diluted in isopropyl alcohol to obtain a 1:1,000 dilution of the original concentration. The purpose of the dilution was to mask the odor of the Androstenone, which can be smelled by humans at high concentrations. The spray solution was placed in a metal aerosol can pressurized with propane. A noise making device was also added to the aerosol can. The propellant, when forced through small holes, caused a sound that exceeded 70 decibels.

The efficacy of an aerosol spray composition containing Androstenone was tested in a commercial research facility housing a large number of dogs. A designated person walked the aisles of the kennel with a calm dog on a leash in order to identify those dogs that met the criteria of barking/jumping. The calm dog on the leash was walked in the center aisle between kennels and also sat outside the kennels. To qualify as a test subject, a dog had to repeatedly jump and bark while the calm dog and the person were in the aisle. A total of 15 dogs were chosen as test subjects.

The dogs were separated into two treatment groups. The dogs in treatment group #1 were the control group and were only treated, when observed to be engaging in barking/jumping behavior, with a loud spray that did not contain any Androstenone. The dogs in treatment group #2 were treated, when observed to be engaging in barking/jumping behavior, with a loud spray canister to which the diluted spray composition containing Androstenone had been added. The test period was for 1 minute. Dog barking/jumping was considered "stopped" if the dog did not bark or jump for at least 60 seconds after treatment was administered. In some cases, if the control (placebo) spray did not stop the barking/jumping in a particular dog or it resumed within 60 seconds following the initial treatment, then the dog was treated with the loud spray plus Androstenone.

Table 2 sets forth the treatments and findings with regard to efficacy. When the loud spray alone (placebo) was applied directly in the facial/snout region of the barking/jumping dogs, 44% of the dogs stopped barking and jumping for at least one minute. When the loud spray plus Androstenone was applied directly in the facial/snout region of the barking/jumping dogs, 100% of the dogs stopped barking/jumping for more than one minute and did not resume barking while the evaluators were present.

The dogs in treatment group #1 that did not initially respond to the placebo were re-sprayed with the Androstenone spray. Of these dogs, the re-spray with Androstenone resulted in 83.5% of the dogs remaining calm and not barking/jumping. Twelve dogs in total received the Androstenone spray and 11 dogs were calmer and did not bark or jump after treatment with the test spray, which resulted in an overall efficacy rate of 91.7%. The one dog that did not respond based on this criterion did stop barking/jumping for 40 seconds, but then, although calmer, resumed barking 40 seconds after the Androstenone spray was applied.

TABLE 2

| Results of Androstenone Spray Treatment Tests | | | |
|---|---|---|---|
| Group | Treatment Administered | Number of Dogs in Group | % Effective (no barking/jumping within 1 minute) |
| 1 | Loud spray only (placebo) | 9 | 44.4% |
| 2 | Loud spray plus Androstenone | 6 | 100% |
| 3 | Placebo first, then Androstenone spray | 6 | 83.5% |
| — | Overall Androstenone efficacy | 11 | 91.7% |

The diluted Androstenone was observed to cause an immediate cessation of barking/jumping in dogs and was also observed to make dogs calmer, even appear mildly sedated making them more cooperative to handlers. The results of this test indicated that using Androstenone in a spray on dogs is a useful training tool because the composition containing the INTEROMONE® reduced dog excitability in a safe, humane manner.

Example 3

Determination of the Effects on Heart Rate from Application of Androstenone to Anxious Dogs A study was conducted to determine whether dogs' heart rate increased following application with an aerosol spray containing Androstenone.

An aerosol spray was prepared which contained about 0.1 µg/mL of Androstenone and isopropyl alcohol using the formulation provided in Example 1.

Four dogs determined to be "anxious" were fit with telemetry jackets and transmitters in order to continually monitor heart rate. Dog heart rates were measured for 10 minutes before treatment, 10 minutes following treatment with a control spray (isopropyl alcohol only), and 10 minutes following treatment with the test spray containing Androstenone and isopropyl alcohol.

FIG. 1 illustrates the data obtained on heart rate. The graph sets forth that both the control spray and the Androstenone spray had no significant effect on the heart rate of the dogs.

Example 4

Preparation of a Pump Spray Containing Androstenone and Use on Dogs and Horses A pump spray formulation containing Androstenone can be prepared according to typical industry techniques described above. Table 3 is the list of ingredients that can be used to prepare a liquid spray formulation comprising Androstenone.

TABLE 3

| Pump Spray Formulation with Androstenone | | |
|---|---|---|
| Ingredient | % | grams |
| Androstenone | 0.01 | 0.01 |
| Isopropyl Alcohol | 10.00 | 10.00 |
| Lavender Chamomile frag. #AA101592 | 0.5 | 0.5 |
| D.I. water | 89.49 | 89.49 |
| Total | 100.00% | 100 |

The resultant spray formulation, when sprayed onto the facial/snout region or in the environment of a dog or horse, will cause the animal to exhibit a significant change in behavior towards a calmer demeanor.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of modifying behavior in an animal comprising: administering a pheromone composition to the animal for a period of time, the composition comprising between about 0.001% and about 1% (w/w) of androstenone, or a synthetic version thereof, and between about 0.5% and 99.99% (w/w) of at least one carrier solvent, wherein the amount of androstenone administered to the animal is between about 1.0 pg/mL to about 1.0 g/mL, wherein the animal is selected from the group consisting of a dog, a cat, and a horse, and wherein anxiety, stress, and aggressiveness in the animal is reduced.

2. The method of claim 1, wherein the composition further comprises a propellant.

3. The method of claim 1, wherein the method of administration is inhalation administration.

4. The method of claim 1, wherein the composition is formulated as a spray, an aerosol, a diffuser, or a slow release matrix.

5. The method of claim 4, wherein administering the spray composition and the aerosol composition comprises spraying the animal or spraying the animal's environment with the composition.

6. The method of claim 1, wherein the period of time is at least one second.

7. The method of claim 1, wherein the period of time is at least one week.

8. The method of claim 1, wherein the period of time is at least one month.

9. The method of claim 1, wherein the composition comprises at least one additional pheromone or pheromone composition.

10. The method of claim 1, wherein the composition comprises 0.01% (w/w) Androstenone, 2.0% (w/w) ethanol, and 97.99% (w/w) propane.

11. The method of claim 4, wherein the aerosol composition comprises 0.01% (w/w) androstenone, or a synthetic version thereof, 2.0% (w/w) ethanol, and 97.99% (w/w) propane.

12. The method of claim 4, wherein the spray composition comprises 0.01% (w/w) Androstenone, or a synthetic version thereof, 10.0% (w/w) isopropyl alcohol, 89.49% (w/w) water, and 0.5% (w/w) fragrance.

13. A method of modifying behavior in a dog comprising: administering a pheromone composition to the dog for a period of time, the composition comprising between about 0.001% and about 1% (w/w) of androstenone, or a synthetic version thereof, and between about 0.5% and 99.99% (w/w) of at least one carrier solvent, wherein the amount of androstenone administered to the dog is between about 1.0 pg/mL to about 1.0 g/mL, and wherein anxiety, stress, and aggressiveness in the dog is reduced.

* * * * *